United States Patent
Taylor

(10) Patent No.: US 10,300,248 B2
(45) Date of Patent: May 28, 2019

(54) MEDICAL LINE RETAINING DEVICE AND METHOD OF USING THE SAME

(76) Inventor: Kevin D. Taylor, Colorado Springs, CO (US)

(*) Notice: Subject to any disclaimer, the term of this patent is extended or adjusted under 35 U.S.C. 154(b) by 0 days.

(21) Appl. No.: 13/367,206

(22) Filed: Feb. 6, 2012

(65) Prior Publication Data
US 2012/0216385 A1   Aug. 30, 2012

Related U.S. Application Data

(60) Provisional application No. 61/447,219, filed on Feb. 28, 2011.

(51) Int. Cl.
| | | |
|---|---|---|
| A61B 17/04 | (2006.01) | |
| A61M 25/09 | (2006.01) | |
| A61M 25/02 | (2006.01) | |
| A61B 50/20 | (2016.01) | |

(52) U.S. Cl.
CPC ............ *A61M 25/09* (2013.01); *A61M 25/02* (2013.01); *A61B 50/20* (2016.02); *A61M 2025/024* (2013.01); *A61M 2025/028* (2013.01); *A61M 2025/09125* (2013.01); *Y10T 29/49826* (2015.01); *Y10T 428/24008* (2015.01); *Y10T 428/24017* (2015.01); *Y10T 428/24479* (2015.01)

(58) Field of Classification Search
CPC ............ A61M 25/02; A61M 2025/024; A61M 2025/028; A61M 2025/09125; A61M 5/1418; A61B 46/23; A61B 2046/234; A61B 2046/236
USPC .......... 606/232; 604/172, 178–180; 248/68.1
See application file for complete search history.

(56) References Cited

U.S. PATENT DOCUMENTS

| | | | |
|---|---|---|---|
| 378,408 | A | 2/1888 | Thomas et al. |
| 1,389,304 | A * | 8/1921 | Holmes ............... A41F 11/02 24/21 |
| 3,696,920 | A | 10/1972 | Lahay |
| 3,890,459 | A * | 6/1975 | Caveney ................ 174/101 |
| 4,029,103 | A * | 6/1977 | McConnell ............. 604/179 |
| 4,605,397 | A | 8/1986 | Ligon et al. |
| 4,971,271 | A * | 11/1990 | Sularz ................... 248/68.1 |
| 5,499,976 | A * | 3/1996 | Dalton .................. 604/180 |
| D378,408 | S | 3/1997 | Pyeatt et al. |
| 5,643,717 | A | 7/1997 | Dobkin |
| 6,375,006 | B1 | 4/2002 | Samuels |
| 6,746,466 | B2 * | 6/2004 | Eidenschink ...... A61M 25/0113 604/103.04 |
| 7,229,051 | B2 | 6/2007 | Mailhot, Jr. |
| 7,320,681 | B2 * | 1/2008 | Gillis et al. ........... 604/174 |

(Continued)

FOREIGN PATENT DOCUMENTS

EP   0463718   1/1992

*Primary Examiner* — Katrina Stransky
*Assistant Examiner* — Martin T Ton
(74) *Attorney, Agent, or Firm* — Aspire IP, LLC; Scott J. Hawranek

(57) ABSTRACT

The invention is directed towards a retaining device for retaining at least one medical line. The retaining device includes a flexible body having a top and bottom surface with at least one slot formed in the top surface. The at least one slot extends to a depth greater than the largest medical line the retaining device is destined to be used with. An attachment mechanism is coupled to the flexible body for securing the flexible body to a supportive surface.

17 Claims, 5 Drawing Sheets

(56) References Cited

U.S. PATENT DOCUMENTS

| | | | |
|---|---|---|---|
| 7,457,506 B1 * | 11/2008 | Osborne, II | F16L 3/2235 248/68.1 |
| 7,544,170 B2 | 6/2009 | Williams et al. | |
| D641,052 S | 6/2011 | Hoek | |
| 2003/0132352 A1 | 7/2003 | Weaver | |
| 2006/0041233 A1 * | 2/2006 | Bowen | 604/180 |
| 2006/0237597 A1 * | 10/2006 | D'Andria | F16L 3/223 248/68.1 |
| 2010/0010475 A1 * | 1/2010 | Teirstein et al. | 604/528 |
| 2011/0248125 A1 | 10/2011 | D'Andria | |

\* cited by examiner

MEDICAL LINE RETAINING DEVICE AND METHOD OF USING THE SAME

This application claims the benefit of U.S. Provisional Patent Application No. 61/447,219, filed on Feb. 28, 2011, which is hereby incorporated by reference for all purposes as if fully set forth herein.

BACKGROUND OF THE INVENTION

Field of the Invention

The invention relates to retaining devices and, more specifically, retaining devices for securing medical wires, catheters, guidewires, electrical lines, cables, tubing and other elongated members during medical procedures.

Discussion of the Related Art

Guidewires and catheters are used in a variety of different medical procedures, for example, during angiographic, endovascular, or surgical procedures. Guidewires are typically used to position catheters in a body lumen, for example arteries, veins or natural orifices within a mammal. The leading end portion of the guidewire is typically introduced into the body through an incision or natural orifice and then advanced to the treatment area. A catheter can be threaded over the guidewire, and advanced over the guidewire to the treatment area. A single guidewire can be used to deliver multiple catheters to the treatment area within the body lumen. This is normally accomplished by withdrawing and removing the first catheter from the wire while leaving the leading edge of the wire in place within the body lumen, and then threading a second catheter over the wire and advancing down to the treatment site. Multiple guidewires and catheters can be inserted into the body lumen at the same time.

When the guidewire or a guidewire and catheter combination is placed within the body lumen, a loose trailing end portion extends out of the patient from the entry point. This trailing end portion can be difficult to manage and requires special attention from the medical staff to ensure it does not become contaminated, tangled or confused with other wires in the procedural area.

Therefore, a device and method for retaining the trailing end of guidewires and catheters is desired.

SUMMARY OF THE INVENTION

Accordingly, this invention is directed towards a retention device and method of using the same that substantially obviates one or more of the problems due to limitations and disadvantages of the related art.

An advantage of the invention is to provide an apparatus to securely retain a medical wire to a medical surface while providing ease of loading and removal of the medical wire from the apparatus.

Another advantage of the invention is to provide a simple and secure mechanism for attaching an apparatus to a medical surface.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the invention, as embodied and broadly described, an aspect of the invention is directed towards a retaining device for retaining at least one medical line adjacent a supporting surface. The retaining device includes a flexible body having a top and bottom surface with at least one nonlinear slot formed in top surface and extending to a depth greater than a diameter of the medical line that the retaining device is configured to be used with. An attachment mechanism is coupled to the body and secured to a supportive surface.

Yet another aspect of the invention is directed towards a retaining device for securing a medical line to a substrate, which includes a flexible body having a top surface, a bottom surface, a side surface, and at least one slot is formed in a top surface of the flexible body. The least one slot extends into the flexible body to a distance greater than a diameter of the medical line. An attachment mechanism is coupled to a bottom surface of the flexible body configured to secure the base portion to a substrate.

Still yet another aspect of the invention is directed towards a retaining device to secure a medical line to a substrate. This method includes attaching a retaining device to the substrate, deforming an opening of at least one slot, and arranging a portion of the medical line in this deformed slot to secure the portion of the medical line.

Yet another aspect of the invention is directed towards a medical kit. The medical kit includes a retaining device which has an attachment mechanism coupled to this retaining device and instructions for use. The kit may also include a secondary device, such as, catheter, stent, or other medical device.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide further understanding of the invention, are incorporated in and constitute a part of this specification. They illustrate embodiments of the invention and together with the description serve to explain the principles of the invention.

In the drawings.

DETAILED DESCRIPTION OF THE ILLUSTRATED EMBODIMENTS

Figure 1:
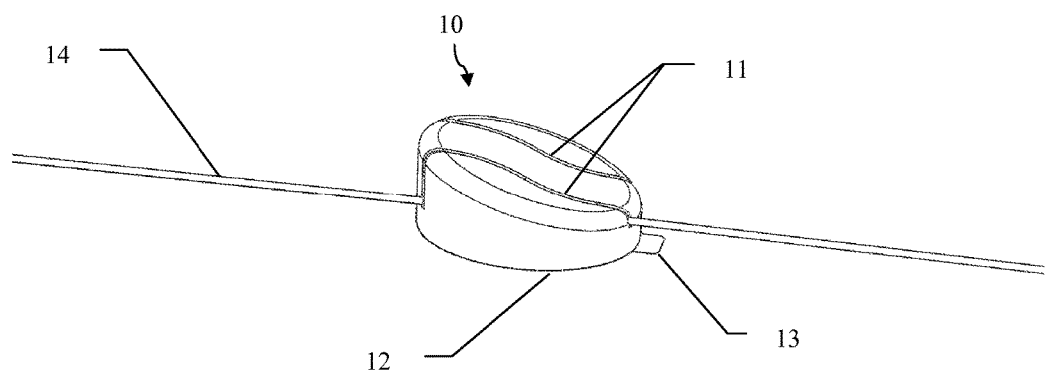
FIG. 1 is a perspective view of a retaining device according to an embodiment of the invention.

An aspect of the invention is directed towards retaining devices and, more specifically, to retaining devices for securing a medical line. The expression "medical line" is used herein to include all kinds of elongated members used during medical procedures, e.g., medical wires, catheters, guidewires, electrical lines, cables, tubing and other elongated members.

In one embodiment, the invention relates to a retaining device for retaining at least one medical line adjacent to a supporting surface. The retaining device includes a flexible body having a top and bottom surface with at least one nonlinear slot formed in the top surface and extending to a depth greater than a diameter of the medical line that the retaining device is configured to be used with. An attachment mechanism is coupled to the body to secure the body to a supportive surface.

In one embodiment, a retaining device for securing a medical line to a substrate includes a flexible body having a top surface, a bottom surface, a side surface, and at least one slot is formed in a top surface of the flexible body. This one slot extends into the flexible body to a distance greater than a diameter of the medical line. An attachment mechanism is coupled to a bottom surface of the flexible body configured to secure the base portion to a substrate.

In one embodiment, a method of using a retaining device to secure a medical line to a substrate includes attaching a retaining device to the substrate, deforming an opening of the at least one slot, and arranging a portion of the medical line in this deformed slot to secure the portion of the medical line.

In one embodiment, a medical kit includes a retaining device which has an attachment mechanism coupled to this retaining device and instructions for use. The kit may also include a secondary device, such as, catheter, stent, or other medical device.

In one embodiment, the flexible body includes a wedge-type shape, however, any geometric shape may be used, such as a square, rectangle, circle, partial sphere, sphere and/or combinations of the same may be used. The flexible body is deformable and constructed from polymer elastomers such as silicone rubber, natural rubber, thermoplastic elastomers and polymer foams such as silicone foams, polyurethane foams, neoprene, and polyolefin foams, and EVA foams.

In one embodiment, the at least one slot includes a plurality of slots. For example, 2 to 10 slots or more. The slot may have a nonlinear configuration to aid with securing the medical line, e.g., a sinusoidal, s-shape and the like. The slot may have constant or variable width as it extends into the flexible body. In a preferred embodiment, the width is configured to be larger than the diameter of the medical wire to be retained. In one embodiment, slot can be a cut slit having a smaller width than the slot may also be used, such as, about 0 inches to about 0.02 inches. In one embodiment, the slot has a "v" shaped opening at or near the top surface to aid in receiving the medical wire. The end portion of the slot may also be angled or curled compared to another portion of the slot, e.g., J shaped end portion.

The at least one slot or slit is configured to extend into the flexible body to a depth greater than a diameter of the medical line that the retaining device is configured to be used with. The slots or slits may also extend into the flexible body at different depths, e.g., a first slot may extend to a first depth and a second slot may extend to a second depth where the first depth is greater than the second depth. Any of the slots may have a tapered configuration, e.g., being wider at one end compared to the other end.

In one embodiment, the at least one slot extends into the flexible body at an angle in a range from about 5 degrees to about 90 degrees measured relative to the top surface. The angle of each slot may be the same or different then the angle of another slot. In a preferred embodiment, the angle is about 80 degrees to about 100 degrees.

In one embodiment, the flexible body includes at least one slot arranged in the side surface extending into the flexible body and in communication with the at least one slot extending from the top surface. In a preferred embodiment, the width of this side slot is greater than the width of the top slot. The side slot can be any geometric shape, e.g., square, rectangular, circular, elliptical, hook shaped, combinations of the same and the like.

In one embodiment, at least one of the slots has a distinguishing marking or color.

In one embodiment, a rigid or semi-rigid plate shaped device is attached to at least a side of the body and covers a portion of the at least one slot. This device is configured to secure the medical line in the at least one slot. The plate may also be able to rotate, thereby locking the medical wire into the slot.

In one embodiment, the attachment mechanism includes a pressure sensitive adhesive secured to the bottom surface of the flexible body.

In one embodiment, the attachment mechanism includes at least one plate shaped structure coupled to a bottom surface of the flexible body. The plate shape structure includes at least one movable tab cut out of a portion shaped structure. The at least one movable tab may include any type geometry, e.g., trapezoidal, square, triangle, angled edges, rectangle, pentagon, hexagon, and/or combinations of the same. In a preferred embodiment, the tab includes three sides. A void or cut out portion remains in the plate shaped structure.

In one embodiment, the attachment mechanism may include a slot mechanism as described with reference towards U.S. Pat. No. 7,229,051, which is hereby incorporated by reference as if fully set forth herein.

In one embodiment, the attachment mechanism may be a securing device as described in U.S. Pat. No. 1,389,304, which is hereby incorporated by reference as if fully set forth herein.

Reference will now be made in detail to an embodiment of the present invention, example of which is illustrated in the accompanying drawings.

FIG. 1 illustrates a retaining device according to an embodiment of the invention. Referring to FIG. 1, the retaining device 10 is configured to hold medical lines.

Figure 2:
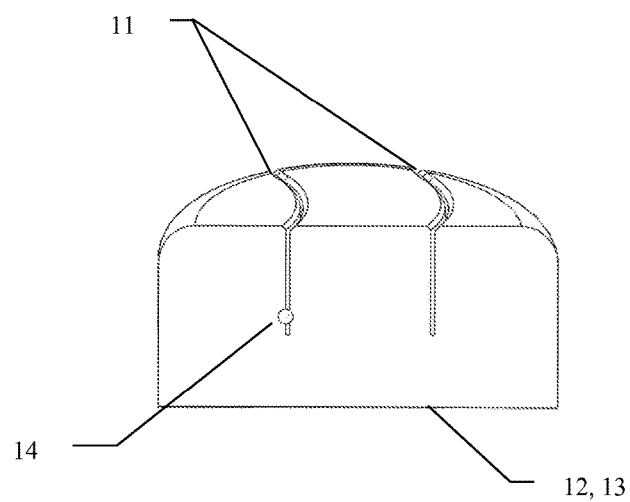
FIG. 2 is a cross-sectional view of the retaining device of FIG. 1 across line 1-1.

As shown in the drawings, medical line retaining device 10 generally includes a flexible body with top and bottom surfaces containing at least one nonlinear slot 11 formed in the top surface. The device may include an attachment mechanism 12 coupled to the body for attaching the retaining device to a substrate. As shown in FIGS. 1 and 2, the retaining device 10 includes a wedge shaped flexible body with 2 sinusoidal shaped slots 11 in the top surface and extending toward the bottom surface. The flexible body is composed of a flexible and compressible material such as a polymer elastomer or polymer foam. These materials flex to allow entry into the slot or slit where the medical line is larger than the slot width. They also allow for greater retention of the line as the material compresses around the line, particularly around the curves in the slot, and thus produce more holding friction due to the increased surface contact.

The slots 11 are dimensioned smaller than the medical line 14 and in a preferred embodiment have a v-shaped opening where they meet the top surface to facilitate entry of the medical line 14 in the slot. In this embodiment the perimeter surface of the body is ellipticalshaped and substantially perpendicular to the bottom surface. The perimeter surface may be any geometric configuration. The attachment mechanism 12 is a pressure sensitive adhesive attached to the bottom surface with a protective liner 13 over the adhesive. Other attachment mechanisms may be used. For example, retaining device 10 could be attached to a heavy, draping pad such as a mouse pad. Mouse pads are typically made with flexible, heavy polymers such as rubber, neoprene rubber, silicone, and silicone foam. A mouse pad holds to a surface without sliding due to weight, a large contacting surface area, a textured contacting surface area, and high coefficient of friction of the before mentioned materials. Alternatively, retaining device 10 could be a unitary structure with sufficient weight and surface area to hold it to the surface without sliding.

In use, a protective liner 13 is removed from pressure sensitive adhesive 12 and retaining device 10 is attached to a supportive substrate, such as a surgical drape, surgical table, bed sheet or the like, via the adhesive material. Medical line 14 is pressed into slot 11 by inserting it into the upper most section of the slot 11 first and then guiding and pulling slightly into the remainder of the slot. During insertion, the flexible material surrounding the slots moves or is deformed to accept the medical line 14, and then forms around the medical line 14 to retain it within the device 10. Retention occurs both by mechanical and/or frictional mechanisms. Mechanical mechanism is due to the body material physically surrounding the medical line 14 and preventing it from moving out of the slot 11. Frictional forces come from at least two sources, the body material pressing into the medical line 14, and the straightening force of the medical line 14 pressing into the curves of the slot 11. To remove, the medical line 14 is simply pulled upward at a force exceeding the mechanical and frictional forces holding the line in the medical slot 11.

Figure 3:
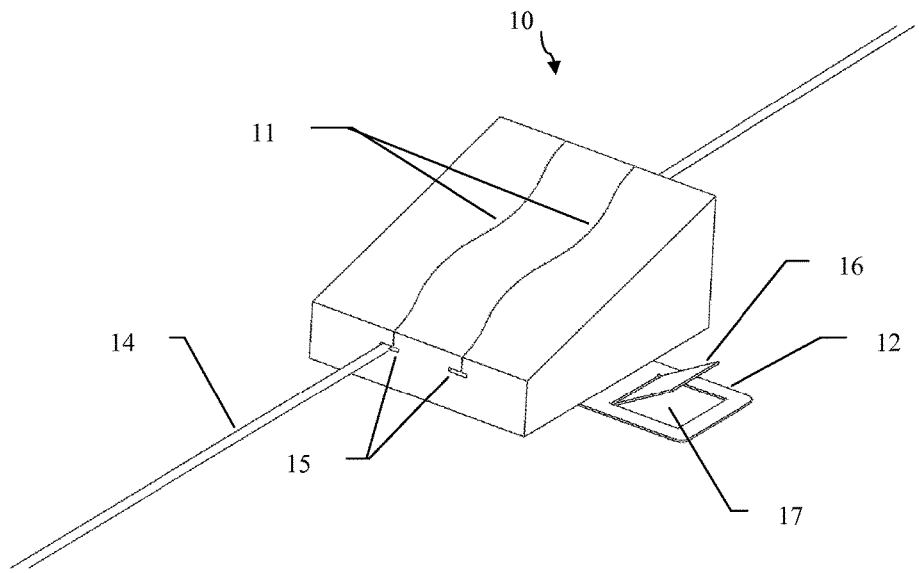
FIG. 3 is a perspective view of another embodiment of the invention.

FIG. 3 illustrates another embodiment of the invention. Referring to FIG. 3, the retaining device 10 includes a wedge shaped body with a rectangular shaped perimeter and has two sinusoidal shaped slits 11 in the top surface and extending towards the bottom surface so that slit depth (from the top surface) is greater than the diameter of the medical device 14. The slits 11 are thin cuts made into the body and width to a distance in of about 0 inches to about 0.02 inches or greater. Two slots 15 extend from the front surface to the back surface. These slots 15 communicate with and are perpendicular with slits 11. Slot 15 height is preferably larger than the largest diameter medical line to be used and width is preferably aligned with and dimensioned the same as the maximum amplitude of the sinusoidal slots 11. Alternately, slot 15 could be a slit or a round orifice.

In use, the medical line 14 is pressed into the slits 11 and moved to the bottom of the slits, the straightening force of the line 14 will cause the line to move into slots 15, thereby providing additional retention to secure line 14 into retaining device 10.

In this embodiment, the attachment mechanism 12 is attached to the bottom surface and extends out one side of the device 10. The attachment mechanism 12 is configured to secure the retaining device 10 to a substrate, e.g., table, bed sheet, a medical drape, gown and the like. The attachment mechanism 12 includes a plate shaped structure overlapping and attached to the bottom surface by an adhesive or other suitable fixing unit, e.g., screw, rivet, and the like. In this embodiment, it is configured to extend from a perimeter of the retaining device 10 and has an integral rectangular or square tab 16 removed from the plate shaped structure extending from the perimeter.

The tab 16 has three sides and a bend on the remaining side connected to attachment mechanism 12 and angled up from the plate structure top surface. Below the bent tab 12 is a rectangular or square orifice 17 in the attachment mechanism 12 approximately the same size as the tab. The tab may have at least one protrusion for aiding securement to the substrate, e.g., a barb. Other types of attachment mechanisms may also be used.

Figure 4:
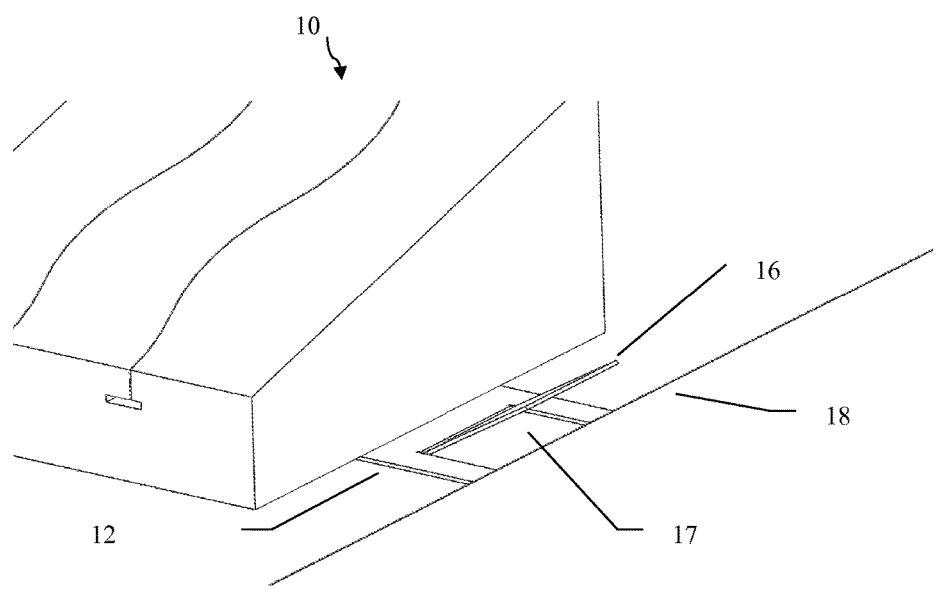
FIG. 4 is a partial, perspective view of an attachment mechanism shown in FIG. 3.

Referring now to FIG. 4, an edge or folded edge of a sheet 18 may be placed partially over the orifice 17 and under the tab 16. To secure the retaining device 10 to the sheet 18, the tab 16 is pushed down and through the orifice 17 and slightly below the plane of the bottom portion of the attachment means 12, wedging the sheet 18 between the tab 16 and orifice 17.

Figure 5:
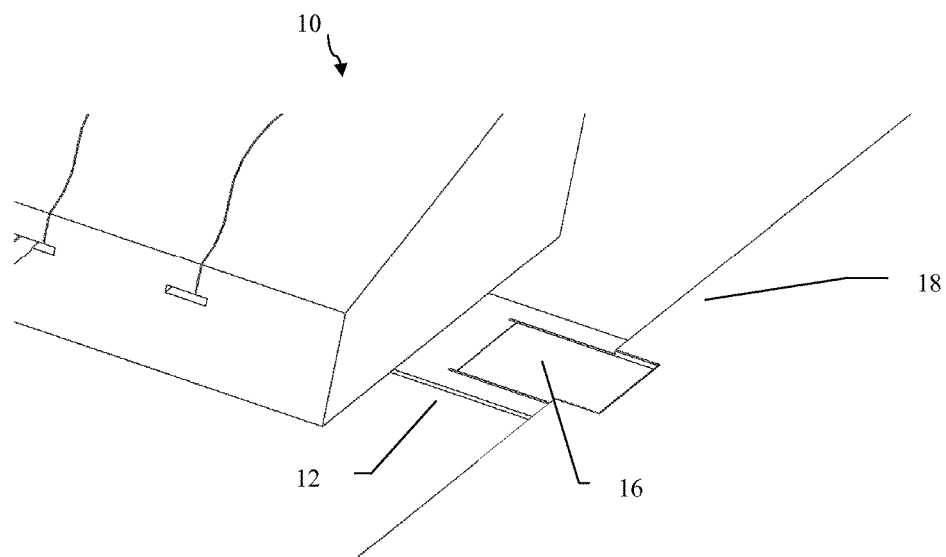
FIG. 5 is a partial, perspective view of the attachment mechanism shown in FIG. 4.
Figure 6:
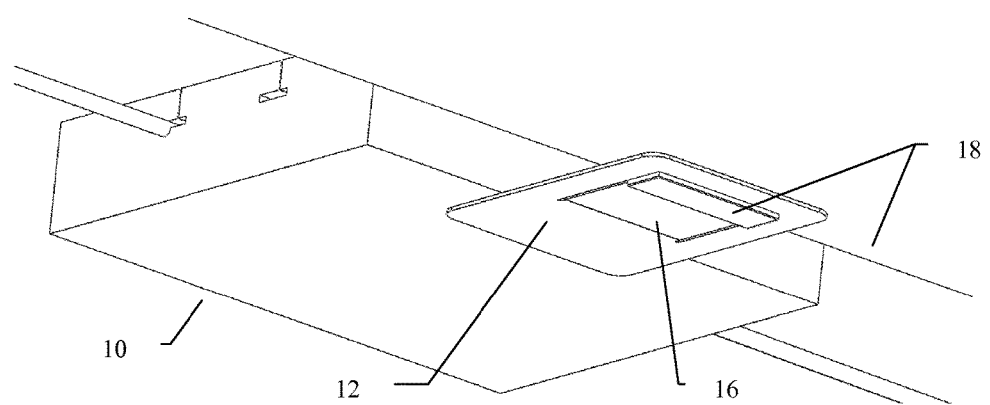
FIG. 6 is an interior, partial, perspective view of the attachment mechanism shown in FIG. 5.

FIGS. 5 and 6 illustrate a substrate 18 in the locked position as viewed from above and below. This embodiment provides a simple, secure means for securing the retaining device to a sheet, drape, or gown. To disengage the substrate 18, the tab 16 is moved back out in the other direction. Other advantages of this attachment mechanism is that it can be combined with an adhesive mechanism as shown in FIGS. 1 and 2 to provide increased utility to secure to many different supporting surfaces.

Figure 7:
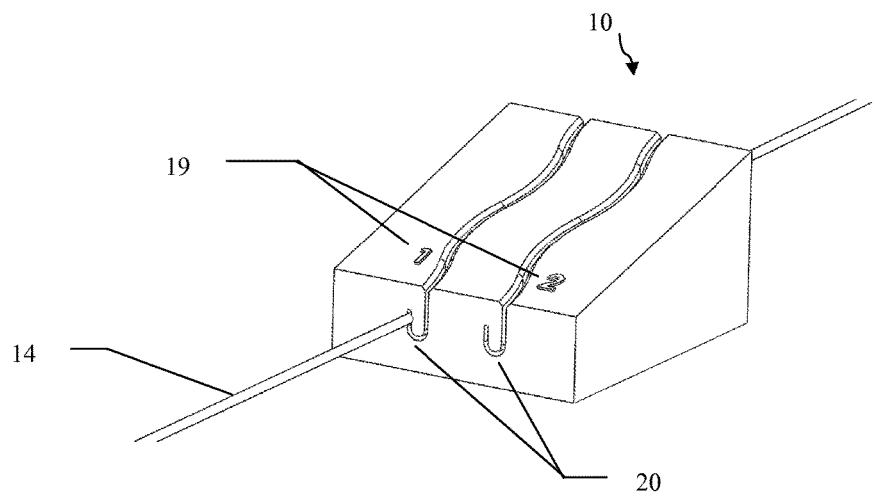
FIG. 7 is a perspective view of another embodiment of the invention.

FIG. 7 illustrates another alternative embodiment of the invention. Referring to FIG. 7, the retaining device 10 includes markings 19 on the top surface next to slots 11 to help identify multiple medical lines 14. The slots could be color coded. Retaining device 10 contains j-shaped slots 20 on the front surface communicating with the sinusoidal slots 11 and they extend perpendicular toward the back surface. The end of the J slot is aligned with the top of the first curve in slot 11 such that the end of the "J" will enter slot 11 at the before mentioned point. This creates a finger shaped projection at the bottom of slot 11 where the line 14 can be manually placed to obtain maximum retention.

Figure 8:
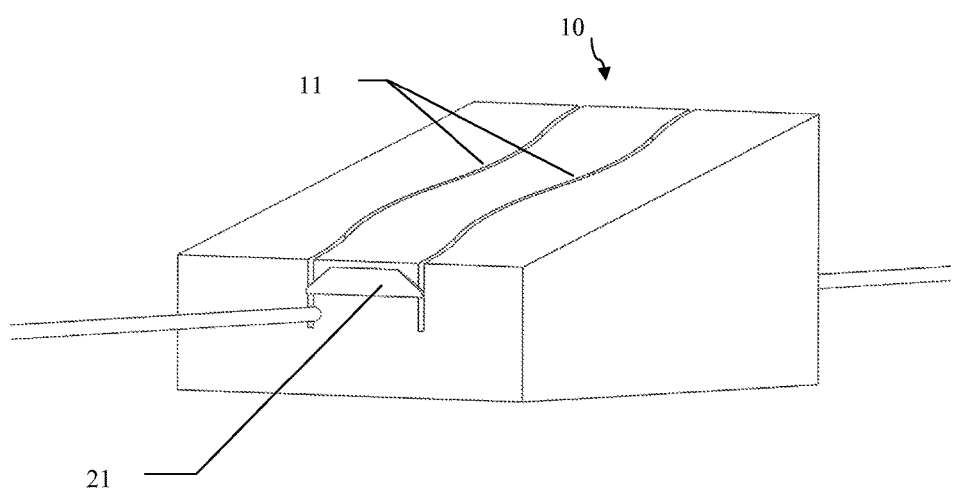
FIG. 8 is a perspective view of another embodiment of the invention.

FIG. 8 illustrates another embodiment of the invention. Referring to FIG. 8, the retaining device 10 includes slots 11 formed in a deformable material. A plate structure 21, e.g., isosceles trapezoid shaped plate, is utilized with the retaining device 10 and adhesively mounted to the front of the retaining device 10 such that the ends extend across the slots 11. The top edge of the plate structure 21 where it crosses the slots 11 has an angled surface which allows a medical line to be easily pushed past ends of structure 11 during insertion of the line 14. The purpose of plate structure 21 is to provide increased retention of the wire 14 and removal of the line 14 is accomplished by manually pushing medical line 11 into the flexible material of the body in order move around ends of structure 21. The plate 21 may also be able to rotate to allow the medical line 11 to be more easily removed.

Figure 9:
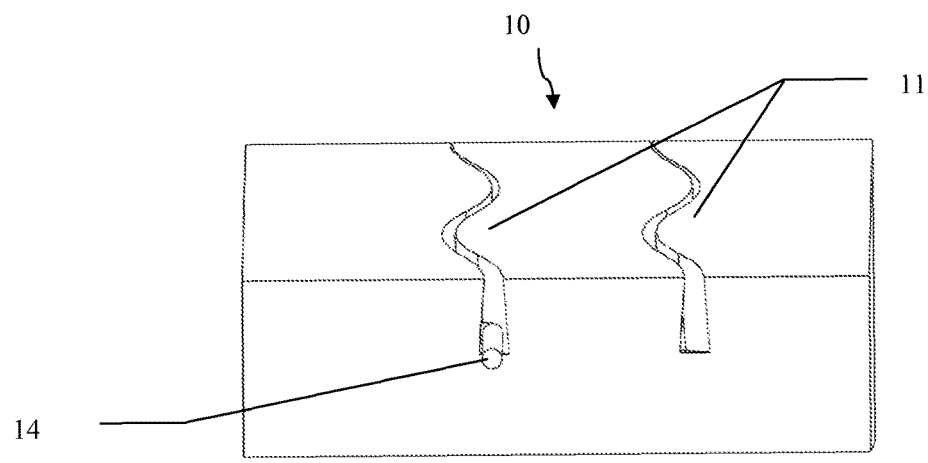
FIG. 9 is a front view of another embodiment of the invention.

FIG. 9 illustrates another embodiment of the invention. Referring to FIG. 9, the retaining device 10 includes slots 11 in a nonlinear configuration. The slots 11 have a tapered cross section, e.g., the slot width is greater at the bottom than at the top.

Figure 10:
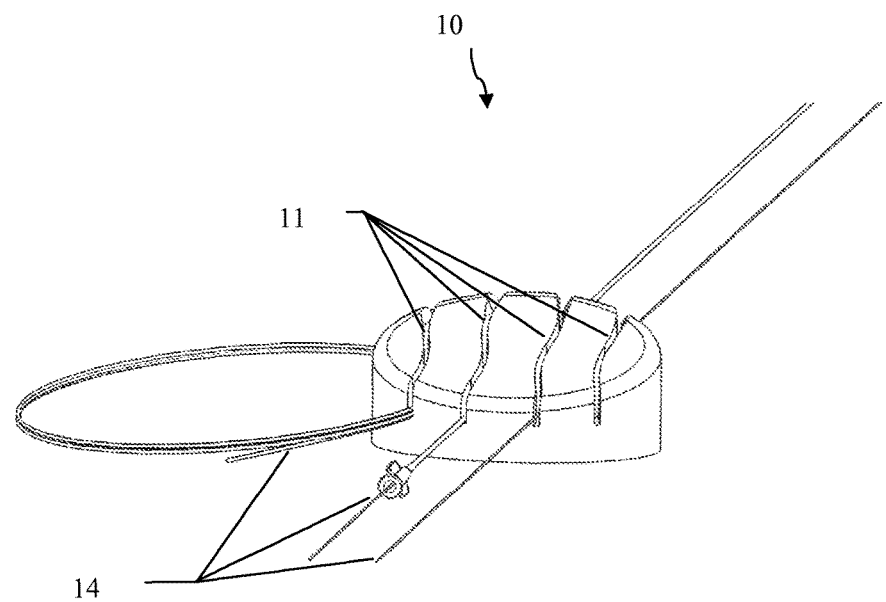
FIG. 10 is a perspective view of another embodiment of the invention

FIG. 10 illustrates another embodiment of the invention.

Referring to FIG. 10, the retaining device 10 includes a wedge shaped body with an elliptical shaped perimeter and four sinusoidal shaped slots 11 in the top surface. Each of the four sinusoidal slots extend toward a bottom surface body. In a preferred, embodiment, this distance or slot depth from the top surface is greater than a diameter or portion of the medical device 14 to be retained and the slots 11 width are sized to be greater than a diameter or portion of a medical device 14 to be retained. In a preferred embodiment, each of the slots contain a V-shaped opening cut into the slots near the top portion of the wedge to aid in receiving a medical device 14. The V-shaped opening runs parallel to the bottom surface and are collinear with the slots. It is noted that the width and depth of each slot may be different with respect to each other.

The medical devices 14 shown in FIG. 10 include a coiled guidewire, a catheter, and a straight guidewire. The wider slots in this embodiment have the advantage of easier loading of the medical device as the material does not need to be deformed to insert the medical device. Retention is accomplished by the friction caused by the bending forces of the medical device against the sinusoidal shaped slot walls. The may also be slot in a sidewall of the shaped body.

EXAMPLES

Without intending to limit the scope of the invention, the following examples illustrate how various embodiments of invention may be made and/or used.

Example 1

In this example, a retaining device similar to FIG. 10 was designed using CAD software (SolidWorks) with the following characteristics. The device was formed as an elliptical shaped measuring 3.9 inches by 2.5 inches. The top surface was angled at 25 degrees to the bottom surface and height of 0.8 inches in the front and 1.9 inches in back. The top surface perimeter was rounded to a radius of 0.15 inches. Four sinusoidal slots, spaced 0.8 inches apart on the top surface, extended to a depth of 0.6 inches from the bottom surface. A slot width of 0.080 inches at the bottom and drafts outward at a 2 degree angle to top surface. The sinusoidal slots include S shaped slots including four connected curves having a 1.40 inch curve with 0.80 inch centerline aligned vertically. The slots lots are symmetrical across horizontal centerline and mirror images across vertical centerline. A 50 degree, horizontal chamfer is cut co-linear with the slots to a depth of 1.7 inch from a bottom surface for middle slots and 1.6 inches from a bottom surface for the edge slots.

The SolidWorks file was saved as a .STL file format and used by stereolithography software to generate information needed to produce 3D models on stereolithography machines. The file was sent to Morpheous Prototypes of Torrence, Calif. to create a mold by Stereolithography and casting the part. After forming, the mold surface was sanded and polished. A two-part RTV silicone rubber having a 25 A durometer was mixed and poured into the mold, allowed to cure for 24 hours and then removed from the mold. The resulting device weighed 0.4 lbs and had a base surface area of 7.7 in.

The inventions and methods described herein can be viewed as a whole, or as a number of separate inventions that can be used independently or mixed and matched as desired. All inventions, steps, processes, devices, and methods described herein can be mixed and matched as desired. All previously described features, functions, or inventions described herein or by reference may be mixed and matched as desired.

It will be apparent to those skilled in the art that various modifications and variations can be made in the present invention without departing from the spirit or scope of the invention. Thus, it is intended that the present invention cover all of the modifications and variations of this invention provided they come within the scope of the appended claims and their equivalents.

What is claimed is:

1. A retaining device for securing a medical device to a substrate, comprising:
   a flexible elliptical shaped body comprises a flexible material having
   a top surface,
   a bottom surface,
   a first side surface region substantially perpendicular to the bottom surface and the top surface,
   a second side surface region substantially perpendicular to the bottom surface and the top surface, the first side surface region spaced apart from the second side surface region,
   a first slot arranged in a top surface of the flexible elliptical shaped body extending from the first side surface region to the second side surface region, and
   a second slot arranged in a top surface of the flexible elliptical shaped body extending from the first side surface region to the second side surface region;
   wherein the first slot has a starting point and an end point relative to the top surface, the starting point starts on a top surface of the flexible elliptical shaped body and extends to the end point and the end point terminates directly adjacent to an interior portion of the flexible elliptical shaped body and the first slot extends from a first side surface region to the second side surface region, the first slot comprises a non-linear slot in an "S" type shape relative to the top surface,
   wherein the second slot has a starting point and an end point relative to the top surface, the starting point starts on a top surface of the flexible elliptical shaped body and extends to the end point and the end point terminates directly adjacent to an interior portion of the flexible elliptical shaped body and the second slot extends from a first side surface region to the second side surface region, the second slot comprises a non-linear slot in an "S" type shape relative to the top surface,
   wherein at least one of the first slot and the second slot extends into the flexible elliptical shaped body at an angle from about 80 degrees to about 100 degrees relative to the top surface and to a distance greater than a diameter of the medical device,
   wherein at least one of the first slot and the second slot has a constant width from the starting point to the end point and is dimensioned to hold the medical device substantially in place,
   wherein the flexible elliptical shaped body is configured to deform upon application of external pressure on the retaining device to open the first slot and the second slot to allow for insertion of the medical device into either the first slot or the second slot; and
   an attachment mechanism coupled to a bottom surface of the flexible elliptical shaped body, the attachment mechanism configured to secure the flexible elliptical shaped body to a substrate,
   wherein the attachment mechanism comprises a rectangular base plate having a first side, a second side, third side, fourth side, an interior portion oriented between the first side, second side, a third side and a forth side, and a tab portion oriented within the interior portion, the tab portion comprising a first tab side, a second tab side, a third tab side, and a bend coupled to the interior portion of the rectangular base plate, wherein the bend is configured to allow the tab portion to move between an open position and a closed position, and wherein in the open position an orifice in an interior portion of the rectangular base plate is configured to receive a portion of the substrate and in the closed position the orifice is substantially closed.

2. The device of claim 1, wherein the at least one slot width is smaller than the diameter of the medical device to be retained.

3. The device of claim 2, wherein the medical device comprises at least one of a guide wire, a catheter, an electrical line, a cable, and a tubing.

4. The device of claim 1, wherein the flexible elliptical shaped body further comprises a slot arranged in the side surface extending into the flexible elliptical shaped body in communication with at least one of the first slot and the second slot.

5. The device of claim 1, wherein the tab portion comprises at least one barb.

6. The device of claim 1, wherein the flexible elliptical shaped body comprises a material selected from the group consisting of polymer elastomer, polymer foam and combinations thereof.

7. The apparatus of claim 1, wherein at least one of the first slot or the second slot has a tapered configuration extending into the depth of the flexible material.

8. The device of claim 1, wherein at least one of the first slot and the second slot has an end portion comprising a J type shape.

9. The device of claim 1, wherein the substrate is selected from the group consisting of a table, drape, sheet, and gown.

10. The device of claim 1, further comprises a plate structure movably coupled to a side surface of the flexible elliptical shaped body, the plate structure movable from a first position to a second position and configured to cover at least a portion of the first slot or the second slot in a closed position.

11. The device of claim 10, wherein the plate structure has a trapezoidal shape.

12. The device of claim 1, wherein the flexible elliptical shaped body comprises an identification marking near the at least one of the first slot and the second slot configured to identify the medical line.

13. The device of claim 1, wherein the flexible elliptical shaped body comprises a sufficient weight to hold on the substrate and prevent sliding off the substrate when the device is used.

14. The device of claim 13, wherein the flexible elliptical shaped body comprises a weight of 0.4 lbs.

15. The device of claim 1, wherein the first slot and the second slot are color coded.

16. A retaining device for securing a one or more guidewires to a substrate, comprising:
a flexible elliptical shaped body having a concave top surface, a flat bottom surface, a side surface substantially perpendicular to the bottom surface and the top surface, at least four slots in a top surface of the flexible elliptical shaped body, wherein each of the four slots extend from the top surface towards a bottom surface and terminates at an end point within the flexible elliptical shaped body, wherein each of the four slots extend at an angle from about 80 degrees to about 100 degrees relative to the top surface and to a distance greater than a diameter of the one or more guidewires, wherein each slot has a constant width, wherein the width of each slot is smaller than an external dimension of the one or more guidewires and has a substantially S-type shape, wherein the flexible elliptical shaped body is configured to deform upon application of an external pressure on the retaining device to open each of the slots to allow for insertion of the one or more guidewires and wherein each slot is configured to prevent the one or more secured guidewires from moving and retaining the one or more guidewires to the substrate; and an attachment mechanism configured to secure a bottom surface of the flexible elliptical shaped body to a substrate, wherein the attachment mechanism comprises a rectangular base plate coupled to a bottom surface of the flexible elliptical shaped body, wherein the rectangular base plate comprises an interior portion arranged within an external dimension of the rectangular base plate, the rectangular base plate comprising a tab portion, the tab portion comprising a first side, a second side connected to the first side, a third side connected to the second side, and a bend portion connected to the second side, the third side and the rectangular plate, the tab portion is arranged within the internal dimensions of the rectangular plate, the tab portion movably coupled to the rectangular base plate with the bend portion, the tab portion movable between an open position and a closed position, in the open position an orifice is configured to receive a portion of the substrate and the orifice is orientated with the interior portion of the rectangular plate; and a plate structure arranged on the side surface of the flexible elliptical shaped body configured to cover at least one of the slots in a first orientation.

17. A retaining device for securing a medical line to a substrate, comprising:
a deformable elliptical shaped body having a top surface, a bottom surface, a side surface substantially perpendicular to the bottom surface and the top surface, at least four slots arranged in a top surface of the deformable elliptical shaped body, each slot has a sinusoidal shape, the slots are symmetrical across a horizontal centerline and mirror images across a vertical centerline;

wherein each of the at least four slots extend from a starting point on the top surface to an end point within the deformable elliptical shaped body at an angle in a range from about 80 degrees to about 85 degrees relative to the top surface, wherein each of the at least four slots comprise a constant width from the starting point to the end point that terminates directly into the deformable elliptical shaped body, the width has a dimension smaller than an external dimension of the medical line, wherein the deformable elliptical shaped body is configured to deform upon application of an external pressure on the retaining device to open at least one of the four slots to allow for insertion of the medical line; and an attachment mechanism configured to secure a bottom surface of the flexible elliptical shaped body to a substrate, wherein the attachment mechanism comprises a rectangular base plate coupled to a bottom surface of the flexible elliptical shaped body, wherein the rectangular base plate comprises an interior portion arranged within an external dimension of the rectangular base plate comprising a tab portion, the tab portion comprising a first base portion movably coupled to a portion of the rectangular base plate, a first side portion extending from the first base portion and a second side portion extending from the first base portion and an end portion substantially perpendicular to the first side portion and the second side portion, the tab portion movable between an open position and a closed position, in the open position an orifice oriented within an internal dimension of the rectangular base plate, the orifice is configured to receive a portion of the substrate.

* * * * *